(12) United States Patent
Motoyama et al.

(10) Patent No.: US 9,001,362 B2
(45) Date of Patent: Apr. 7, 2015

(54) REPOSITORY-BASED PRINT SERVICES

(75) Inventors: Tetsuro Motoyama, Cupertino, CA (US); Tomohito Shimizu, Cupertino, CA (US)

(73) Assignee: Ricoh Company, Ltd., Tokyo (JP)

( * ) Notice: Subject to any disclaimer, the term of this patent is extended or adjusted under 35 U.S.C. 154(b) by 74 days.

(21) Appl. No.: 13/620,618

(22) Filed: Sep. 14, 2012

(65) Prior Publication Data

US 2014/0078544 A1  Mar. 20, 2014

(51) Int. Cl.
*G06F 3/12* (2006.01)
*G06F 19/00* (2011.01)
*G06F 21/62* (2013.01)
*H04L 29/06* (2006.01)
*H04L 29/08* (2006.01)

(52) U.S. Cl.
CPC ............ *G06F 3/1204* (2013.01); *G06F 3/1206* (2013.01); *G06F 3/1238* (2013.01); *G06F 3/126* (2013.01); *G06F 3/1267* (2013.01); *G06F 3/1288* (2013.01); *G06F 19/30* (2013.01); *G06F 21/6218* (2013.01); *H04L 63/083* (2013.01); *H04L 63/102* (2013.01); *H04L 67/02* (2013.01)

(58) Field of Classification Search
None
See application file for complete search history.

(56) References Cited

U.S. PATENT DOCUMENTS

| | | | | |
|---|---|---|---|---|
| 5,913,208 A * | 6/1999 | Brown et al. | | 707/706 |
| 8,373,876 B2 * | 2/2013 | Watanabe | | 358/1.15 |
| 8,626,727 B2 * | 1/2014 | Paknad et al. | | 707/694 |
| 2002/0019827 A1 * | 2/2002 | Shiman et al. | | 707/200 |
| 2002/0161603 A1 * | 10/2002 | Gonzales | | 705/1 |
| 2003/0078880 A1 * | 4/2003 | Alley et al. | | 705/38 |
| 2013/0110547 A1 * | 5/2013 | Englund et al. | | 705/3 |
| 2013/0214043 A1 * | 8/2013 | Kong et al. | | 235/380 |

FOREIGN PATENT DOCUMENTS

EP          1764714 A1    3/2007

OTHER PUBLICATIONS

European Patent Office, "Search Report" in application No. 13183828.6-1959, dated May 8, 2014, 7 pages.

* cited by examiner

*Primary Examiner* — Paul F Payer
(74) *Attorney, Agent, or Firm* — Hickman Palermo Becker Bingham LLP; Edward A. Becker (57) ABSTRACT

An approach is provided for a service provider to identify documents to include in a client's repository and for the client to print the documents from the client's repository. In an embodiment, a computing device receives authentication information identifying a first user, receives first user information identifying a second user, receives information indicating selection of a one or more particular documents, from a set of one or more documents, and sends document information that at least identifies the one or more particular documents to a repository associated with the second user. A printing device receives second user information identifying the second user, and, in response to receiving the second user information, retrieves the one or more particular documents from the repository based, at least in part, on the second user information. The printing device processes at least one document of the one or more particular documents for printing.

16 Claims, 9 Drawing Sheets

DOCUMENTS FOR THE PATIENT

NAME [____________] ─330

EMAIL [____________] ─332

ID# [____________] ─334

☐ EMAIL REFERENCES?  [READ ID] ─336
   338

SELECT DOCUMENTS:

☐ MAYO CLINIC HEALTHY EATING PLAN  302

☐ DIABETES DIET AND FOOD TIPS  304

☐ DIABETES.ORG MEAL PLANS  306

☐ MEDICINE A USAGE  308

☐ MEDICINE B USAGE AND SIDE EFFECTS  310

☐ MEDICINAL SUPPRESSION OF BLOOD SUGAR  312

☐ DIABETES AND GETTING OFF MEDICATIONS  314

☐ DEFEATDIABETES.ORG SUPPORT GROUPS  316

☐ LIVING WITH DIABETES  318

─ 320

[DONE]

REPOSITORY-BASED PRINT SERVICES

FIELD OF THE INVENTION

The present invention relates to repository-based print services, and, more specifically, to a service provider identifying documents to include in a client's print repository and the client printing the documents from the client's repository.

BACKGROUND

Many times, an individual or entity that provides services ("service provider") to clients must explain detailed concepts to the clients in a limited amount of time. For example, a doctor has a short allotted appointment time in which to explain to a patient medical diagnoses, usage and side effects of prescribed medicines, exercises targeted to aid in a patent's condition, etc. As a further example, a financial professional has a short allotted appointment time in which to explain the implications of certain financial tools, the options that a person has to grow their retirement fund, etc. As yet a further example, an auto mechanic has a limited amount of time to explain suggested fixes or upkeep procedures for a client's automobile, comparisons of certain products for the client's automobile, etc. There are many examples of service providers that are expected to explain relatively complex concepts to clients in a short amount of time.

It can be challenging for a service provider to communicate all of the needed information to a client during the client's allotted time. Even if a service provider has time to thoroughly explain needed information to a client, the client can be overwhelmed by such a conversation and forget key pieces of information. To aid in the communication of needed information, a service provider may have certain pre-printed information on hand to give to a client for the client to read on her own time. However, such pre-printed information can include information that is not tailored to an individual client's situation, which may overwhelm the client and dissuade the client from reading all of the printed information. It would be beneficial to provide a mechanism by which a provider of services may easily provide detailed information to a client that is tailored to the client's particular needs.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

SUMMARY

An approach is provided for a service provider to identify documents to send to a client's repository and for the client to print the documents from the client's repository. In an embodiment, a computing device is configured to receive authentication information identifying a first user, and receive first user information identifying a second user, wherein the first user is different from the second user. The computing device is further configured to receive information indicating selection of one or more particular documents, from a set of one or more documents, and send document information that at least identifies the one or more particular documents to a repository associated with the second user. A printing device is configured to receive second user information identifying the second user, and, in response to receiving the second user information, retrieve the one or more particular documents from the repository based, at least in part, on the second user information. The printing device is further configured to process at least one document of the one or more particular documents for printing. The approach may be implemented as a computer-implemented method, by an apparatus, system or device, or by a computer-readable medium storing instructions which, when processed by one or more processors, implement the approach.

DETAILED DESCRIPTION

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

General Overview

An approach is provided for a service provider to identify documents to send to a client's repository and for the client to print the documents from the client's repository. In an embodiment, a computing device is configured to receive authentication information identifying a first user, and receive first user information identifying a second user, wherein the first user is different from the second user. The computing device is further configured to receive information indicating selection of one or more particular documents, from a set of one or more documents, and send document information that at least identifies the one or more particular documents to a repository associated with the second user. A printing device is configured to receive second user information identifying the second user, and, in response to receiving the second user information, retrieve the one or more particular documents from the repository based, at least in part, on the second user information. The printing device is further configured to process at least one document of the one or more particular documents for printing.

According to an embodiment, the printing device is communicatively connected to a display device and to a scanner, and the printing device is further configured to receive the second user information via the scanner, display, at a graphical user interface displayed at the display device, data that at least identifies the one or more particular documents, receive a print command via the graphical user interface, and process the at least one document for printing in response to receiving the print command.

According to a further embodiment, the computing device is communicatively connected to a scanner, and the computing device is further configured to receive the first user information via the scanner.

According to a further embodiment, the set of one or more documents includes a first subset of documents that is not editable by the first user, and a second subset of documents that is editable by the first user.

According to yet a further embodiment, the computing device is further configured to browse documents, via a network, at a browser, wherein the browser is configured to receive input from the first user that a particular document currently displayed at the browser should be added to the second subset of documents. The computing device is further configured to include information at least identifying the particular document in the second subset of documents in response to receiving input from the first user that the particular document currently displayed at the browser should be added to the second subset of documents. According to yet a further embodiment, the information at least identifying the particular document includes one or more labels for the particular document.

According to yet a further embodiment, the printing device is further configured to receive an email command, and, in response to receiving the email command, send the one or more particular documents to an email account associated with the second user information.

Repository System Architecture

Figure 1:
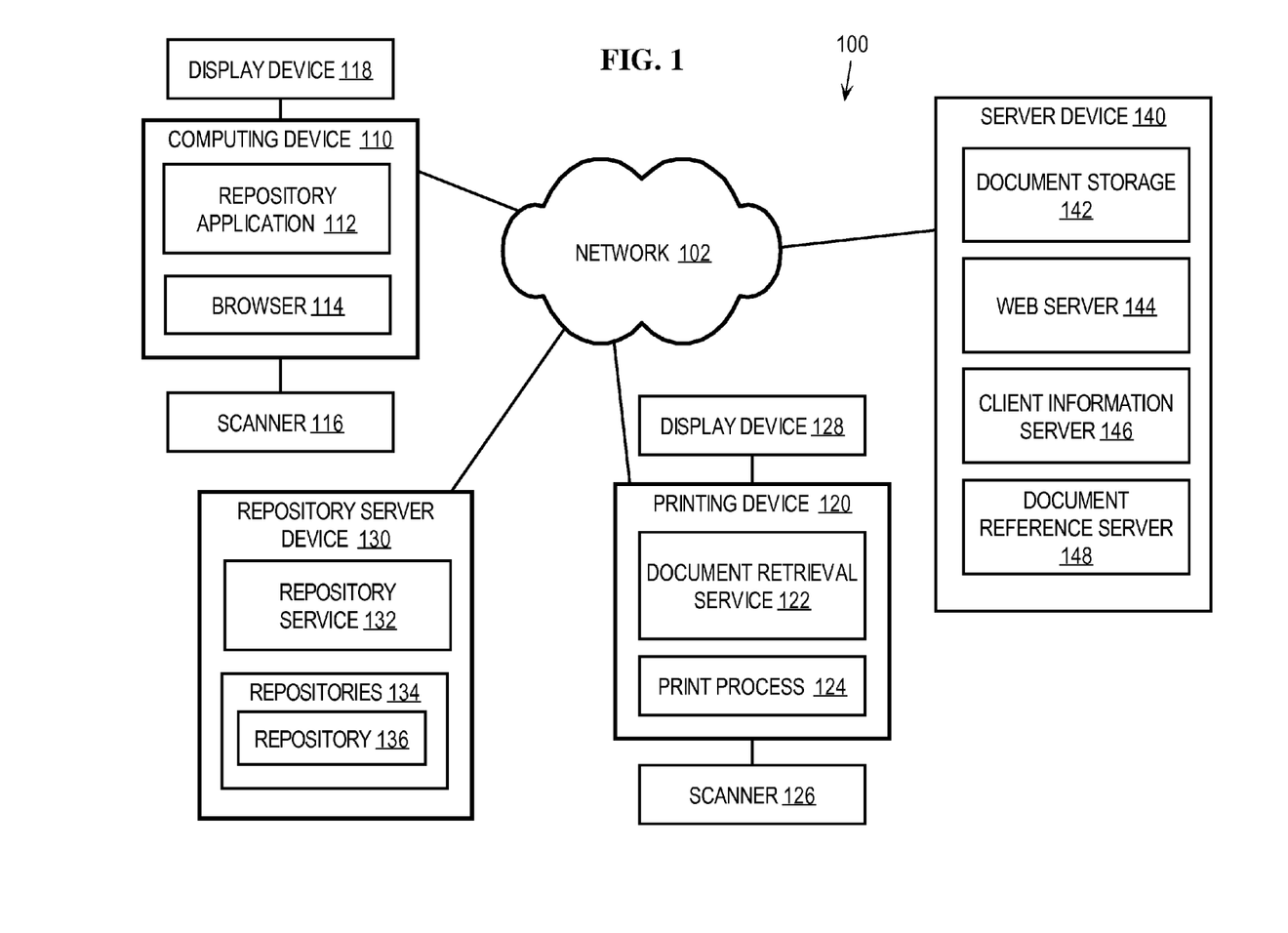
FIG. 1 is a block diagram that depicts an example network arrangement for a service provider to identify documents to send to a client's repository and for the client to print documents from the client's repository.

FIG. 1 is a block diagram that depicts an example network arrangement 100 for a service provider to identify documents to send to a client's repository and for the client to print documents from the client's repository, according to an embodiment of the invention. Example network arrangement 100 includes a computing device 110, a printing device 120, a repository server device 130, and a server device 140 communicatively coupled via a network 102. Example network arrangement 100 also includes scanners 116 and 126, and display devices 118 and 128. Any number of devices, including printing devices, client devices, and other devices, may be included in the network.

Computing device 110 may be implemented by any type of computing device. Example implementations of computing device 110 include, without limitation, workstations, personal computers, laptop computers, tablet computers, personal digital assistants (PDAs), cellular telephony devices, and any type of mobile devices. In example network arrangement 100, computing device 110 is configured with a repository application 112 and a browser 114. As described in more detail below, repository application 112 allows a service provider to edit a list of the service provider's information sources (documents), identifies a client (i.e., via scanner 116), and/or causes selected documents to be stored at a repository of repositories 134 (e.g., repository 136). As also described in more detail below, browser 114 is configured to browse documents, i.e., on the Internet via network 102. In one embodiment of the invention, computing device 110 is configured without browser 114. Computing device 110 may be configured with other mechanisms, processes, and functionality, depending upon a particular implementation.

Printing device 120 may be implemented by any type of device that is capable of communicating with repository server device 130 over network 102, processing print data, and generating printed versions of documents reflected in the print data. In example network arrangement 100, printing device 120 includes a document retrieval service 122 and a print process 124. Printing device 120 may be configured with other mechanisms, processes and functionality, depending upon a particular implementation. The approach described herein is not limited to any particular type of printing device or network configuration. For example, printing device 120 may be a multi-function peripheral (MFP) that includes any combination of printing, copying, facsimile, and scanning capability, etc. Example network arrangement 100 may include multiple printing devices that are capable of retrieving and processing document data from repository server device 130.

Document retrieval service 122 may be implemented by one or more processes configured to receive document data from repository server device 130, as described in more detail below. Print process 124 may be implemented by one or more processes configured to create and/or process print data received from repository server device 130, and to generate a printed version of a document reflected in the print data.

Document retrieval service 122 and print process 124 may be implemented as resident processes on printing device 120. Alternatively, one or more of document retrieval service 122 and print process 124 may be made available to printing device 120 on a removable media or may be implemented at a remote location with respect to printing device 120. Also, document retrieval service 122 and print process 124 may be implemented as plug-ins, or in hardware, software, or any combination of hardware or software, depending upon a particular implementation.

Repository server device 130 may be implemented by any type of computing device that is capable of communicating with computing device 110 and printing device 120 over network 102. In example network arrangement 100, repository server device 130 includes repository service 132, which handles requests to store and/or retrieve documents from repositories 134, as described in more detail below. Repositories 134 may be implemented by any type of storage mechanism capable of maintaining multiple repositories, each of which stores document information and is associated with a particular user. For example, repositories 134 may be implemented by a relational database, an XML database, or any other kind of storage mechanism. Repository server device 130 may be configured with other mechanisms, processes and functionality, depending upon a particular implementation, and the approach described herein. According to an embodiment, repository server device 130 is part of a cloud storage service. For example, the functionality and services provided by repository server device 130 may be provided by one or more cloud services and one or more cloud applications.

Repository server device 130 is depicted in FIG. 1 and described herein as being a separate network element for purposes of explanation only and repository server device 130 may be included on computing device 110 or printing device 120. For example, in an embodiment, printing device 120 is configured with one or more services to perform one or more of the functions attributed to repository service 132 herein.

Network 102 may be implemented with any type of medium and/or mechanism that facilitates the exchange of information between computing device 110, printing device 120, and repository server device 130. Furthermore, network 102 may use any type of communications protocol and may be secured or unsecured, depending upon the requirements of a particular application.

Computing device 110 is communicatively coupled to display device 118 and printing device 120 is communicatively coupled to display device 128. Each of display devices 118 and 128 may be implemented by any type of display device, including Cathode Ray Tubes (CRT), Liquid Crystal Displays (LCD), Light-Emitting Diode (LED) monitors, touch screens, projectors, etc. According to an embodiment, display device 118 is integrated with computing device 110, as in with a tablet computing device. According to an embodiment, display device 128 is integrated with printing device 120, as in with a kiosk printing device.

Further, computing device 110 is communicatively coupled to scanner 116 and printing device 120 is communicatively coupled to a scanner 126. Scanners 116 and 126 may be implemented by any type of device capable of scanning codes and/or documents, including a camera, a bar code scanner, a Quick Response (QR) code scanner, a card reader, a magnetic strip scanner, a device using Near Field Communication, a document scanner, etc.

Server device 140 may be implemented by any type of computing device that is capable of communicating with devices via network 102. Server device 140 is configured with a web server 144 that serves documents in document storage 142 via network 102. Server device 140 is further configured with client information server 146 and document reference server 148. Server device 140 may be configured with other mechanisms, processes and functionality, depending upon a particular implementation, and the approach described herein.

Sending Document Data to a User's Repository

Figure 2:
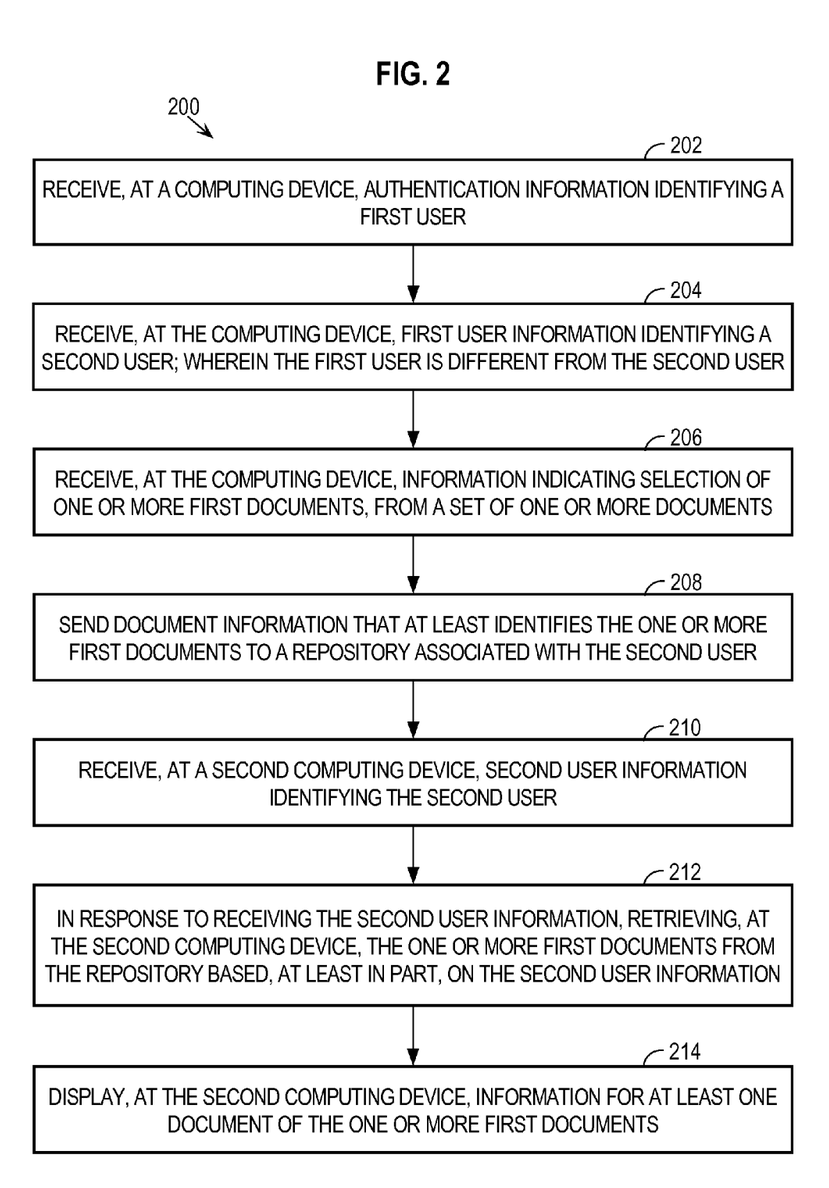
FIG. 2 depicts a flowchart for sending data for a document to a user's repository and displaying the document at a computing device.

FIG. 2 depicts a flowchart 200 for sending data for a document to a user's repository and processing the document for printing at a printing device. The steps of flowchart 200 are depicted and described herein in the context of a doctor service provider and a patient client. This example is non-limiting however, as the steps of flowchart 200 may be applied in many service provider/client contexts. Example contexts include, without limitation, the auto mechanic/client context, the professor/student context and the architect/client context, etc.

At step 202, authentication information identifying a first user is received at a computing device. For example, repository application 112 on computing device 110 receives authentication information identifying a particular doctor. In an embodiment, the authentication information is a user name and password entered via a graphical user interface (GUI) at display device 118. In another embodiment, the authentication information is obtained from an employee card that is swiped or scanned at scanner 116.

Repository application 112 uses the authentication information to retrieve a list of documents associated with the doctor identified in the authentication information. This list of documents, described in more detail below, may be stored in any location according to embodiments of the invention, including at computing device 110, at repository server device 130, etc.

In another embodiment, the authentication information is used to log the doctor into computing device 110. In this embodiment, part or all of the list of documents may be stored at computing device 110 and part or all part of the list of documents may be retrieved from repository server device 130.

Figure 3A:
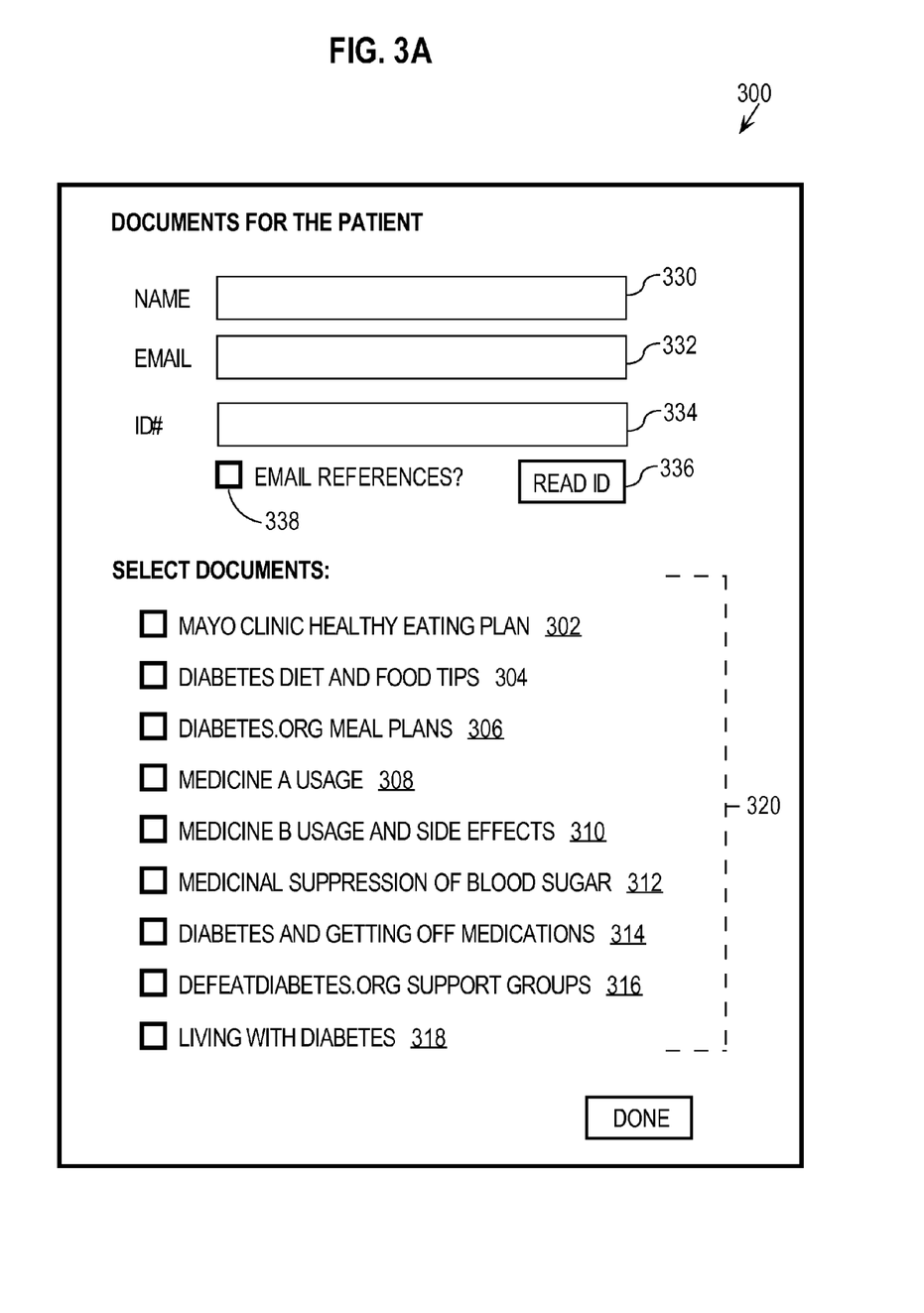
FIG. 3A depicts a graphical user interface configured to be populated with a patient's name, an email address, and an identification number.

At step 204, first user information identifying a second user is received at the computing device, wherein the first user is different from the second user. For example, a patient of the particular doctor may scan a patient identifier code (e.g., on an arm bracelet, on an identification card of the patient, a bar code, QR code, or other electronically-identifiable information on a paper provided to the patient, etc.) at scanner 116 to produce scan data that identifies the patient. GUI 300 of FIG. 3A is displayed at display device 118 and depicts a graphical user interface configured to be populated with a patient's name (at field 330), an email address (at field 332), and an identification number (at field 334).

Figure 3B:
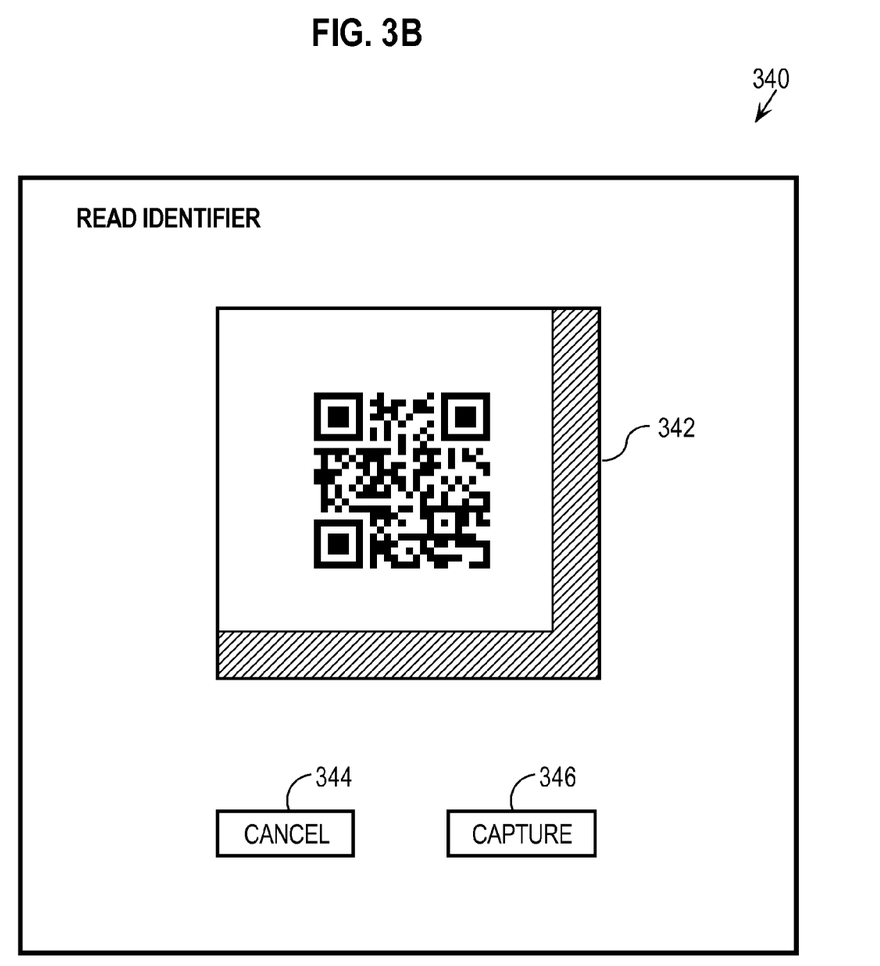
FIG. 3B depicts a graphical user interface configured to capture identifying information for a client via a scanner.

A doctor may acquire information identifying a patient by activating read id button 336. According to an embodiment, activation of read id button 336 causes computing device 110 to display, at display device 118, GUI 340 depicted at FIG. 3B. Field 342 represents an image within the field of scanner 116, which may be a camera communicatively coupled to, or integrated with, computing device 110. The example of FIG. 3B depicts identifying information, i.e., a QR code, within the field of scanner 116. A user may activate capture button 346 to capture identifying information within the field of scanner 116. The user may also activate cancel button 344 to return to GUI 300.

Figure 5:
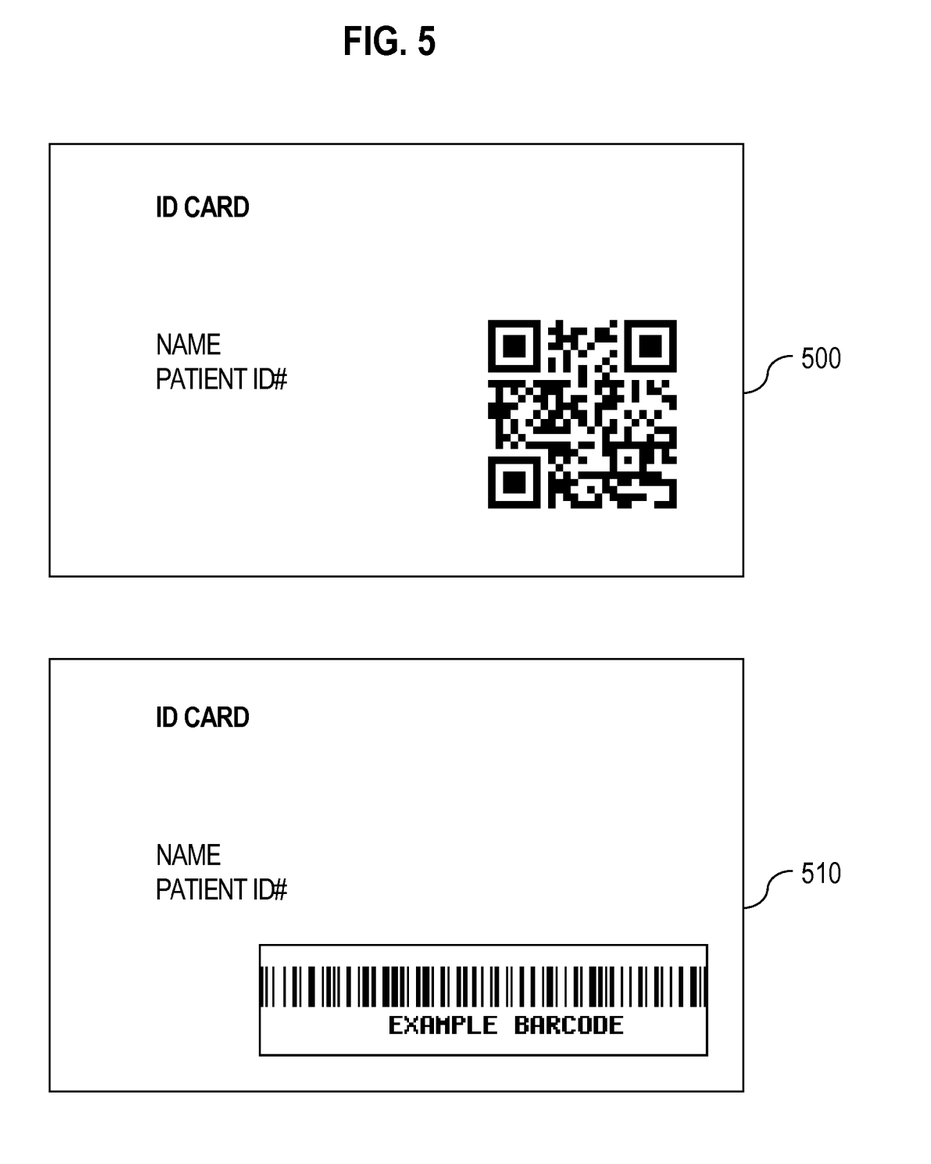
FIG. 5 depicts user identification cards.

FIG. 5 depicts user identification cards 500 and 510 that have identifying information thereon: a QR code and a barcode, respectively. Other forms of identifying information may be used within embodiments. A user may hold one of user identification cards 500 and 510 within the field of scanner 116, as depicted in GUI 340.

Repository application 112 receives the scan data from scanner 116. Repository application 112 extracts information encoded in the identifying information and sends the decoded information to client information server 146 at server device 140. Client information server 146 returns, to repository application 112, information for the patient corresponding to the decoded information. Repository application 112 may populate one or more of fields 330-334 of GUI 300 with information obtained from client information server 146.

As a further example, the doctor may enter information identifying the user into GUI 300 at one or more of fields 330-334. In this example, repository application 112 receives the identifying information via GUI 300. The identified patient is recorded by repository application 112 to be the current patient.

At step 206, information indicating selection of one or more first documents, from a set of one or more documents, is received at the computing device. For example, repository application 112 receives information indicating selection of one or more documents from a list of documents associated with the doctor, e.g., the list of documents retrieved with the doctor's authentication information described above. An example document list 320 that is associated with the doctor is depicted in FIG. 3A. Repository application 112 may cause document list 320 to be displayed at GUI 300 at display device 118, and the doctor selects one or more documents from document list 320 that pertain to the doctor's patient. Repository application 112 receives information indicating the documents selected by the doctor via the GUI.

To illustrate, the current patient was recently diagnosed with diabetes and the doctor selects document 302 that provides information about a healthy eating plan. The doctor may also select documents that include instructions for using a particular medicine (e.g., document 308), information about support groups for diabetics (e.g., document 316), etc.

At step 208, document information that at least identifies the one or more first documents is sent to a repository associated with the second user. For example, repository application 112 sends information for one or more documents (e.g., document 302), selected by the doctor, and information identifying the current patient to repository service 132 for storage at a repository (in repositories 134) that is associated with the patient. Information for document 302 that is sent to repository service 132 may identify document 302 via a Uniform Resource Locator (URL) that identifies the location of document 302 via network 102 or in a storage medium of computing device 110. Further, the information for document 302 may include one or more of the document file, print data for document 302, a rendering of document 302, and other information. According to an embodiment, repository service 132 creates a rasterized image, a pdf file, or other printable data in repository 136 for document 302.

Repository service 132 receives the information sent by repository application 112 and identifies, using the information identifying the patient, the repository of repositories 134 associated with the patient to be repository 136. Repository service 132 stores the information for document 302 in repository 136.

According to an embodiment, the doctor has the option to send one or more documents from document list 320 to an email address (e.g., at checkbox 338 of GUI 300). The email address may be known based on the information for the current patient retrieved via scanner 116, associated with a user's profile either stored at computing device 110, repository server device 130, or at another server device not shown in FIG. 1. Further, the email address may be input at computing device 110 in connection with the request to email the one or more documents.

Processing a Repository Document for Printing

Once the doctor has stored documents at the patient's repository, the documents are available for the patient to print at the patient's leisure. A patient may choose to access the patient's repository to view and/or print the documents, e.g., at a kiosk that includes printing device 120 (described in further detail below) at the exit of a hospital at which the patient visited the particular doctor.

Returning to flowchart 200 of FIG. 2, at step 210, second user information identifying the second user is received at a second computing device. The second computing device may be printing device 120, or may be another computing device. To illustrate, document retrieval service 122 at printing device 120 receives, via a GUI displayed at display device 128, information identifying the patient of the previous example. In this example, the user may type into text fields in the GUI the patient's name, patient identifier, and/or other identifying information.

As another example, document retrieval service 122 receives information identifying the patient via scanner 126. In this example, the patient scans an identification card, bar code, QR code, or other electronically-identifiable information at scanner 126 to produce scan data that identifies the patient. Document retrieval service 122 determines the information identifying the patient from the scan data.

At step 212, in response to receiving the second user information, the one or more first documents is retrieved at the second computing device from the repository based, at least in part, on the second user information. For example, document retrieval service 122 sends a request to repository service 132 for the documents stored at a repository associated with the patient accompanied by information identifying the patient. Repository service 132 identifies repository 136 as the repository that is associated with the patient based on the received patient information. Repository service 132 sends information that at least identifies all documents in repository 136 to document retrieval service 122.

At step 214, information for at least one document of the one or more first documents is displayed at the second computing device. The second computing device may comprise at least one of: a projector, and a display device. For example, printing device 120 (the second computing device) is communicatively connected to display device 128. Printing device 120 causes information for documents stored at repository 136 to be displayed at display device 128. The displayed information includes one or more of: information identifying the documents, content of the documents, one or more attributes of the documents, etc.

According to an embodiment, document retrieval service 122 displays the list of documents at a GUI at display device 128. In addition to the list of documents, the GUI at display device 128 may include a mechanism for each document in the list by which a user may (a) select the document, (b) display a rendering of the document via display device 128, (c) delete the document, (d) email the document to a particular email address, (e) print the document, etc. The email address may be entered by the user via the GUI at display device 128, or may be included in the user information received at printing device via scanner 126. Also, printing device 120 may have access to additional information about the user at a remote server (not shown in FIG. 1). Further, the GUI displayed at display device 128 may include a mechanism by which all selected documents are deleted, or printed, or displayed, or emailed.

According to an embodiment, the second computing device comprises a printing device, or, in other words, the second computing device is communicatively connected to a printer. In this embodiment, the second computing device processes at least one document of the one or more first documents for printing. For example, the patient activates a mechanism by which one or more documents displayed at display device 128 are printed. Thus, in this example, a print command for the one or more documents is issued to print process 124. In an embodiment, the print command of all documents in the patient's repository is implied based on receiving the second user information identifying the second user.

In response to the explicit or implied print command, print process 124 processes for printing the documents associated with the print request. According to one embodiment, the information stored at a repository for a particular document includes a URL for the document, and does not include print data or the document's file. In this embodiment, print process 124 retrieves, based on the URL, information for the document to be printed and generates print data from that information. According to another embodiment, the information stored at a repository for a particular document includes print data for the document. In this embodiment, print process 124 processes the print data retrieved from the repository for printing. According to yet another embodiment, the information stored at a repository for a particular document includes a document file. In this embodiment, print process 124 generates print data from the document file retrieved from the repository and processes that for printing.

In the embodiment where the data is stored at repository 136 as print data or a document file, the data for the document is frozen at the point that it was stored in the repository. This may be beneficial if the document is a web page, which may be changed by the owner of the web page at any time. Also, the owner of a web page may change the URL to the web page after the URL is stored at the repository. On the other hand, in the embodiment where repositories 134 store the documents as URLs and not as print data or a document file, any updates to the information in the document would be included in the document at the time that it is retrieved by document retrieval service 122, which allows any updates to be included in the printed data for the client.

In an embodiment where the user has the option to email a document from printing device 120, document retrieval service 122 receives an email command for a particular document, e.g., through a GUI displayed at display device 128. In response to the email command, document retrieval service 122 sends a document file for the particular document to an email address associated with the patient. The email address may be typed into the GUI by the patient, or may be retrieved based on the user's information. According to an embodiment, in connection with an email command, the document may be "printed" to a pdf file and the pdf file is sent to the email address. According to an embodiment, the selected documents are processed for physical printing by print process 124 at the time that the documents are emailed.

In an embodiment, documents that have been printed or emailed are erased from repository 136 as soon as the user logs out of printing device 120.

Print Kiosk

In one embodiment, printing device 120 and scanner 126 are part of a kiosk with display device 128 as the kiosk display. Such a kiosk may be placed at the exit of the service provider's building for a client to use before the client leaves the building. A default screen displayed at display device 128 may include instructions for the client, e.g., "Print the documents from your doctor here". According to this embodiment, display device 128 may be a touch screen. Any input device may be included in the kiosk. For example, the kiosk may include a physical print button that a client presses to print all of the documents in the client's repository. In the case of a physical print button, the display device 128 may simply display messages to the user, such as the following: "You have at least one document to print. Please press the print button to print your documents."; or "You have no documents to print. Please call this number if you believe that you should have documents to print."

Further, the kiosk may allow clients to selectively print a subset of the documents from the client's repository. For example, the display device 128 may display a list of the documents currently stored on the client's repository and allow the client to select and print particular documents from the list of documents displayed. This may be helpful, for example, if the client has already obtained a copy of one or more documents from another source or otherwise does not wish to print all of the documents.

Non-Kiosk Printing

According to one embodiment, a user other than the patient interacts with printing device 120. For example, a member of the service provider's staff may send to document retrieval service 122 the second user information (according to step 210 of flowchart 200), e.g., as part of checking out the client. According to this embodiment, display device 128 is associated with a computing device (e.g., the staff member's computer—not shown in FIG. 1), which is communicatively coupled to printing device 120. The service provider staff member may submit the client's information via a GUI at display device 128 or via scanner 126.

The service provider's computing device may run an application that communicates the client's information to document retrieval service 122, e.g., via an Application Programming Interface (API). Further, the service provider's computing device may access a particular web page, via a browser running on the machine, through which the staff member may submit client information to document retrieval service 122 according to step 210. Document retrieval service 122 retrieves documents from repository 136 using the client's information and proceeds as described above, including processing one or more of the retrieved documents for printing, if applicable in a particular context.

Service Provider Editable Document List

Document list 320 of FIG. 3A is an example of a list of documents that is created by a service provider user, such as the doctor of the examples given above. Document list 320 is associated with the service provider user and may be stored at repository server device 130, computing device 110, or at any other location within the embodiments of the invention. Repository application 112 may retrieve document list 320 in connection with authenticating the service provider user. Each document of document list 320 includes one or more of the following: a URL, print data, a document file, other identifying information, a nickname, a timestamp, one or more labels, etc.

The service provider user may add a document to document list 320 in various ways within the embodiments of the invention. In embodiments, the service provider user enters information identifying a document, e.g., a URL for the document, into a GUI displayed at display device 118. The provided GUI may allow the service provider user to browse to a location on a storage medium of computing device 110 and add the locally-stored document to document list 320. To illustrate, the service provider user scans a printed article and saves the scan data to the memory of computing device 110. The service provider user then browses to the location of the saved scan data to add the scanned article to document list 320. Repository application 112 receives the information entered into the GUI, and adds the information as a new document to document list 320.

According to further embodiments, browser 114 is configured to add information identifying the document that is currently displayed at browser 114 to document list 320. To illustrate this embodiment, the plug-in may cause a button to be displayed in the GUI of the browser that, when pressed, records information for the document currently displayed in browser 114 to document list 320. The plug-in may cause a pop up GUI to be displayed that requests further information about the document, such as a nickname, one or more labels for the document, etc. Any information that the user supplies in response to this request is stored in document list 320 for the document. Browser 114 or repository application 112 may cause print data to be created for the document and include this print data with the information for the document in document list 320.

According to an embodiment, browser 114 is further configured to send a particular document being displayed in browser 114 directly to the current client's repository. For example, browser 114 requests information for the current client repository (repository 136) from repository application 112. In an embodiment, repository application 112 stores information identifying repository 136 as the current client repository, and all operations on a client repository are performed on the current client repository 136 until repository application 112 receives information indicating that repository 136 is no longer the current client repository (e.g., because the client session has ended, the client or service provider has logged out at computing device 110, or information for a new current client repository is sent to repository application 112, etc.). Browser 114 may request further information from the service provider user prior to sending the document to the current client repository 136. Browser 114 may also cause the document to be saved to document list 320.

Service Provider Non-Editable Document List

In an embodiment, the service provider user is supplied with a list of documents, in addition to document list 320, that is not editable by the service provider. To illustrate, a particular service provider user is managed under a certain department at a hospital. The department administrators provide, to the particular service provider user, a list of documents to be displayed with document list 320 (as depicted by document list 424 in FIG. 4 described in further detail below). This list of documents that are provided by the department may be documents that the administrators consider important to be available to the service providers.

The list of documents that is not editable by the service provider user may be associated with a setting for the service provider user (e.g., the service provider user's department) and retrieved by repository application 112 in connection with authenticating the service provider user. Furthermore, an administrator may construct such a list of documents in a similar manner to the way that the service provider user constructs document list 320, as described above.

In one embodiment, browser 114 includes a mechanism by which a service provider user may nominate the document currently displayed at browser 114 to be included in the administrator's list of documents. In response to receiving activation of the mechanism, browser 114 sends information identifying the document to repository application 112, which emails the request to an email address associated with the administrators.

Document List Display

Repository application 112 causes display device 118 to display a GUI, such as GUI 300 of FIG. 3A, that includes the document lists for the service provider user, including document list 320. In an embodiment, the list of documents that are not editable by the service provider user is also depicted in GUI 300. According to this embodiment, a list of documents such as list 400 of FIG. 4 (that includes both provider document list 422 and a department document list 424) would replace document list 320 in GUI 300.

In GUI 300, the documents are listed using the associated nicknames for the documents. In one embodiment, if no nickname is provided for a particular document, then the document is displayed using the URL (or other identifying information) for the document.

GUI 300 may include an option to view more information for one or more of the documents, activation of which displays further information stored in connection with the documents. Further, GUI 300 may include an option to open a document, e.g., in browser 114 or in another program associated with the document's file. GUI 300 may include an option to update print data or a document file for a particular document, which updates the stored print data or document file based on source information for the document.

In GUI 300, the documents may be displayed in groups based on one or more of a source of the document (user editable list/non-editable list, Internet domain, etc.), document labels, a document type, etc. To illustrate, document list 400 of FIG. 4 includes several document groups, where each group may be expanded or contracted as with a tree structure or folder/file structure display. Accordingly, GUI 300 may include expand all and/or contract all mechanisms which expand or contract all of the groupings, respectively.

Figure 4:
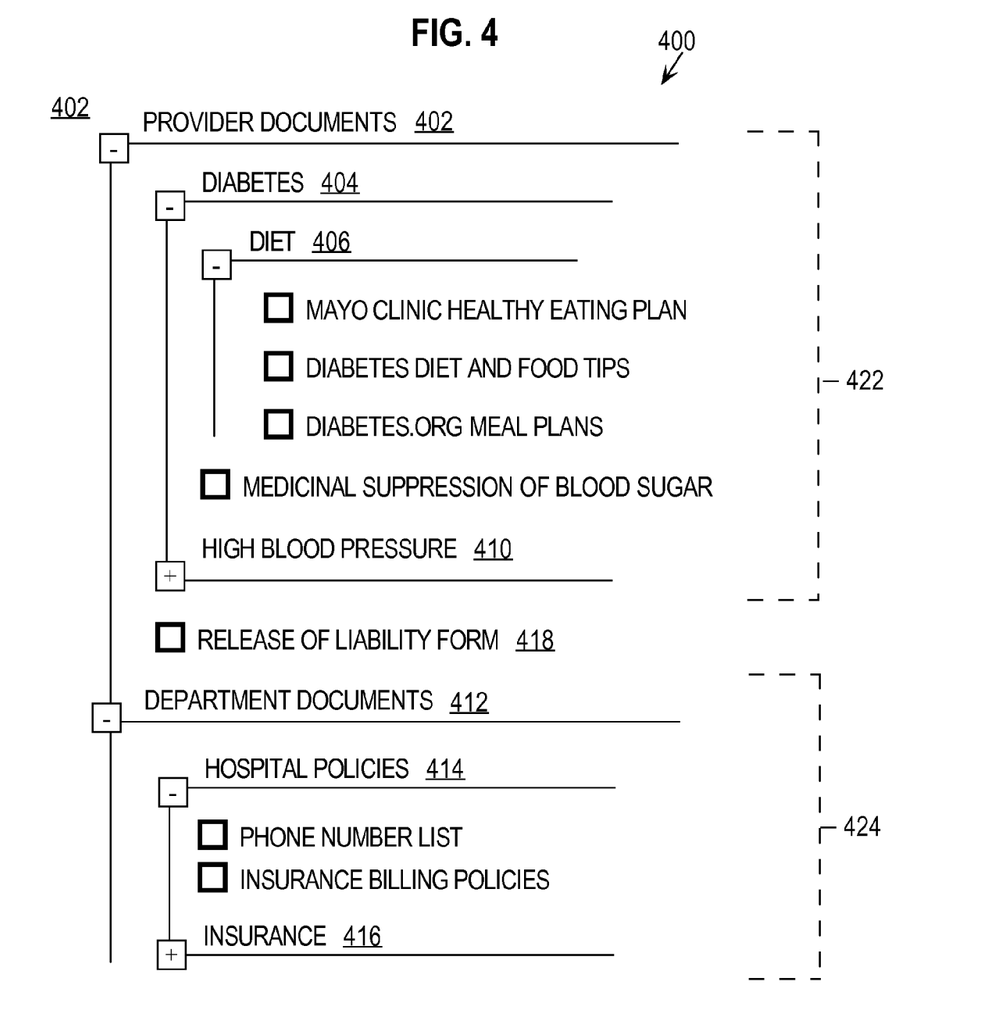
FIG. 4 depicts a document list.

Document list 400 includes a document group labeled by label 402, which includes the documents added by, and editable by, the service provider user. Document list 400 further includes a documents group labeled by label 412 that includes documents that are not editable by the service provider user, e.g., documents from administrators of a department for the service provider user.

GUI 300 may also include a mechanism by which the service provider user views a history of the documents sent to the current client repository 136, which may also indicate whether the client has viewed, emailed, or printed documents from the repository.

Document Labels

Document list 400 displays documents grouped by labels 402-416, which are associated with the documents. A document may have zero or more labels associated therewith.

According to an embodiment, document labels are organized in a label hierarchy. In example document list 400, labels 402 and 412 pertain to a first level of labels in the label hierarchy, under which all documents or groups of documents are organized. According to an embodiment, label 402 ("provider documents") and label 412 ("department documents") are labels that are automatically assigned to documents based on whether the document is part of service provider document list 422, or part of document list 424 that is not editable by the service provider user. Other labels may be associated with a document to indicate a source for the document.

Document list 400 also displays groups associated with second-level labels 404, 410, 414, and 416. Because document 418 is only associated with a first-level label, it is displayed at the level of the second-level labels. Furthermore, label 406 is a third-level label. According to an embodiment, application of label 406 automatically applies labels 402 and 404 to the document because labels 402 ad 404 are above label 406 in the label hierarchy.

The service provider user applies labels to documents when the documents are added to a document list. According to an embodiment, the user types in the labels. According to another embodiment, labels of the label hierarchy are managed in a labels database, e.g., at repository server device 130 or at computing device 110. When the service provider user adds a new document to document list 422 or 320, the service provider user may select one or more labels from one or more drop down lists populated based on the labels database for application to the new document, or may add a new label to the labels database and have that new label applied to the new document. When adding a new label to the labels database, the service provider user indicates a position in the labels hierarchy for the new label.

GUI 300 allows the service provider user to select one or more documents from document list 320 (or document list 400) and send those documents to the current client repository 136. GUI 300 may also include a mechanism by which the service provider user may add all of the documents associated with a particular label to the client's repository. Thus, the service provider user may send all information under a label "basic diabetes information" to a client who has been newly diagnosed with diabetes, and may also send a certain article under a label "specialized diabetes information" that particularly pertains to the client's condition. Furthermore, the service provider user may choose more sophisticated documents for a more sophisticated client and simpler or less-involved documents for a client that is less sophisticated.

Document Selection from a Printed List

A service provider user may not be comfortable with working on computing device 110. Thus, in an embodiment, a service provider user may select one or more documents printed on a piece of paper. For example, document list 320 of FIG. 3A may be printed on a piece of paper and the service provider user may check the boxes next to the documents that the service provider user wants in the client's repository. The service provider user may scan the piece of paper using scanner 116 to produce scan data. Repository application 112 identifies the documents selected by the doctor from the scan data, e.g., using an Optical Character Recognition (OCR) application. Repository application 112 causes information for the identified documents to be stored at repository 136, which is the current client repository.

To illustrate, OCR data generated for the paper depicting the one or more documents selected by the service provider may be stored at repository 136. As another example, the OCR data that represents the paper depicting the one or more documents selected by the service provider may be processed and data identifying the one or more selected documents may be stored at repository 136, without necessarily storing data that represents the entire printed document depicting the one or more documents selected by the service provider or storing the one or more selected documents in repository 136.

Further, the client may scan the piece of paper with the service provider user's document selection at scanner 126 and document retrieval service 122 identifies the documents selected by the doctor from the scan data. According to an embodiment, document retrieval service 122 treats the documents identified from the scan data as if the documents were retrieved from the client's repository. According to another embodiment, document retrieval service 122 causes the documents identified from the scan data to be added to a repository associated with the client, and then proceeds with retrieving documents from the client's repository, e.g., repository 136.

Making Documents Available for a Client to Print

Figure 6:
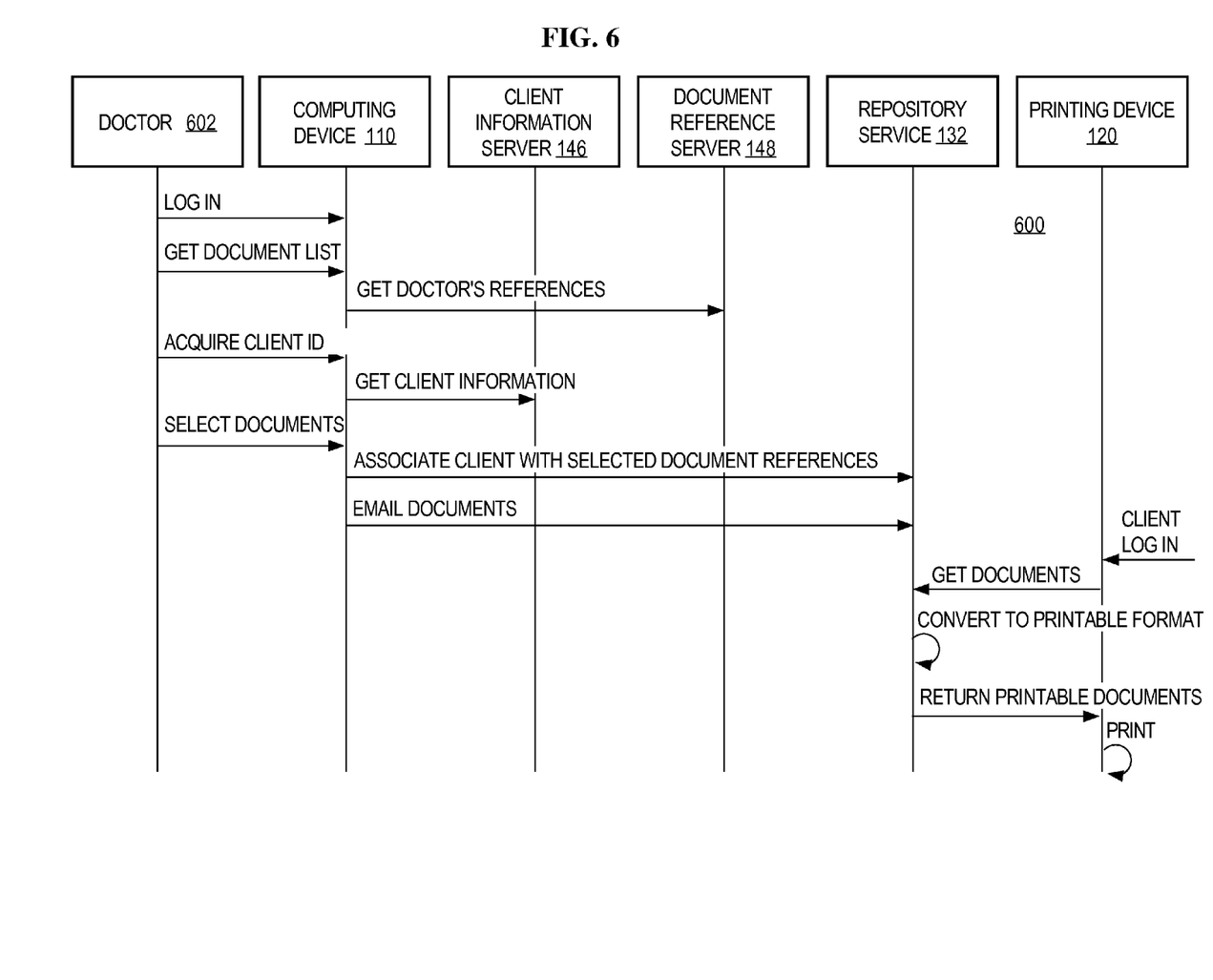
FIG. 6 depicts a flowchart sequencing illustrative events making documents available for a patient to print.

FIG. 6 depicts a flowchart sequencing illustrative events making documents available for a client to print. A doctor 602 logs into computing device 110, i.e., by providing authentication information to computing device 110. Doctor 602 issues a command to retrieve the doctor's document list. For example, the command may be a result of causing display device 118 to display GUI 300 of FIG. 3A, or may be included in a start up routine of computing device 110. As a result of receiving the command to retrieve the doctor's document list, computing device 110 requests document references associated with the doctor from document reference server 148.

A document reference is information identifying a location for a document. Information identifying a location for a document may include a URL for a document accessible via network 102, may include the location of the document in document storage 142, which stores copies of documents that are accessible by document reference server 148, etc. Document storage 142 may include a company's (e.g., a hospital's) standard documents and copyright-cleared documents that may be transmitted to or referred to in a client's repository or email.

Figure 7:
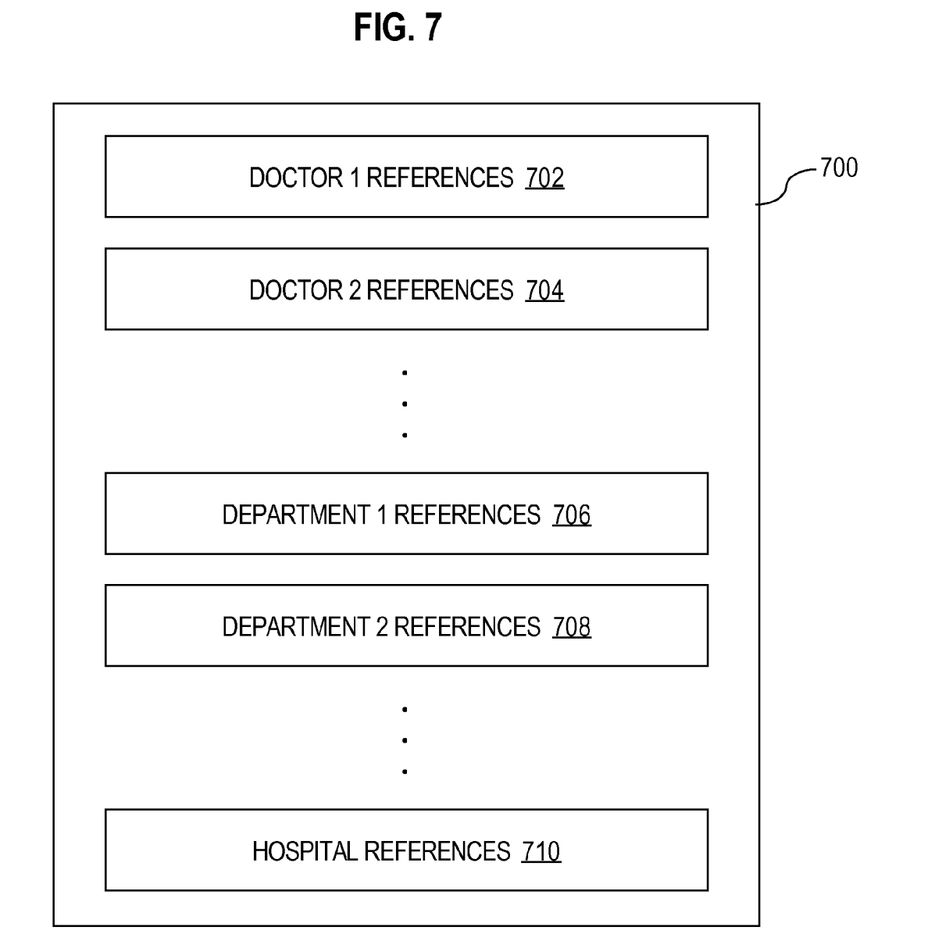
FIG. 7 depicts a repository for document references.

FIG. 7 depicts a repository 700 for document references that is accessible by document reference server 148. Repository 700 may be stored at repository server device 130, server device 140, or at any other location that is accessible by document reference server 148. Repository 700 includes sets of references (e.g., reference sets 702 and 704) that are compiled by individual doctors, sets of references (e.g., reference sets 706 and 708) that are associated with departments of a hospital, and sets of references (e.g., reference set 710) that are the standard documents for the hospital. The levels of granularity depicted in repository 700 are illustrative, and may be adjusted according to a particular implementation. Furthermore, information for multiple entities, such as multiple hospitals, may be included in a document repository such as repository 700.

The request from computing device 110 to retrieve an authenticated doctor's document list includes information about the doctor. Document reference server 148 uses this information to identify the document reference sets associated with the doctor, including doctor-specific document references, document references for a department associated with the doctor, and hospital document references for a hospital associated with the doctor. According to an example, document reference server 148 identifies document reference sets 702, 708, and 710 as references for doctor 602.

Doctor 602 then acquires a client identifier. For example, the doctor may cause computing device 110 to capture identifying information for a client via scanner 116 as described above. Computing device 110 requests client information associated with the acquired identifying information from client information server 146.

Doctor 602 selects documents from the doctor's document list to associate with the identified client. The selected documents may be from any of the doctor's document reference sets (e.g., sets 702, 708, and 710). Computing device 110 sends information for the selected document references to repository service 132 for inclusion into repository 136 associated with the client, also described above.

If selected by doctor 602, computing device 110 causes repository service 132 to email information for the selected documents to the client. The email may include references to the selected documents, may have the selected documents attached thereto, etc. Documents that are stored at document storage 142 may be made available to clients and doctors via web server 144, which serves documents from document storage 142 via network 102.

The client logs into printing device 120, as described above. Document retrieval service 122 at printing device 120 requests documents for the client from repository service 132. Repository service 132 may convert to printable format one or more document references in repository 136, which is associated with the client. For example, to convert a document in repository 136 to printable format, repository service 132 downloads a printable version of a document based on a document reference stored at repository 136. As a further example, repository service 132 creates a rasterized image, a pdf file, or other printable data for a document referred to in repository 136.

Repository service 132 returns printable documents to document retrieval service 122 at printing device 120 for printing. Print process 124 at printing device 120 causes the documents to be printed.

Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 8:
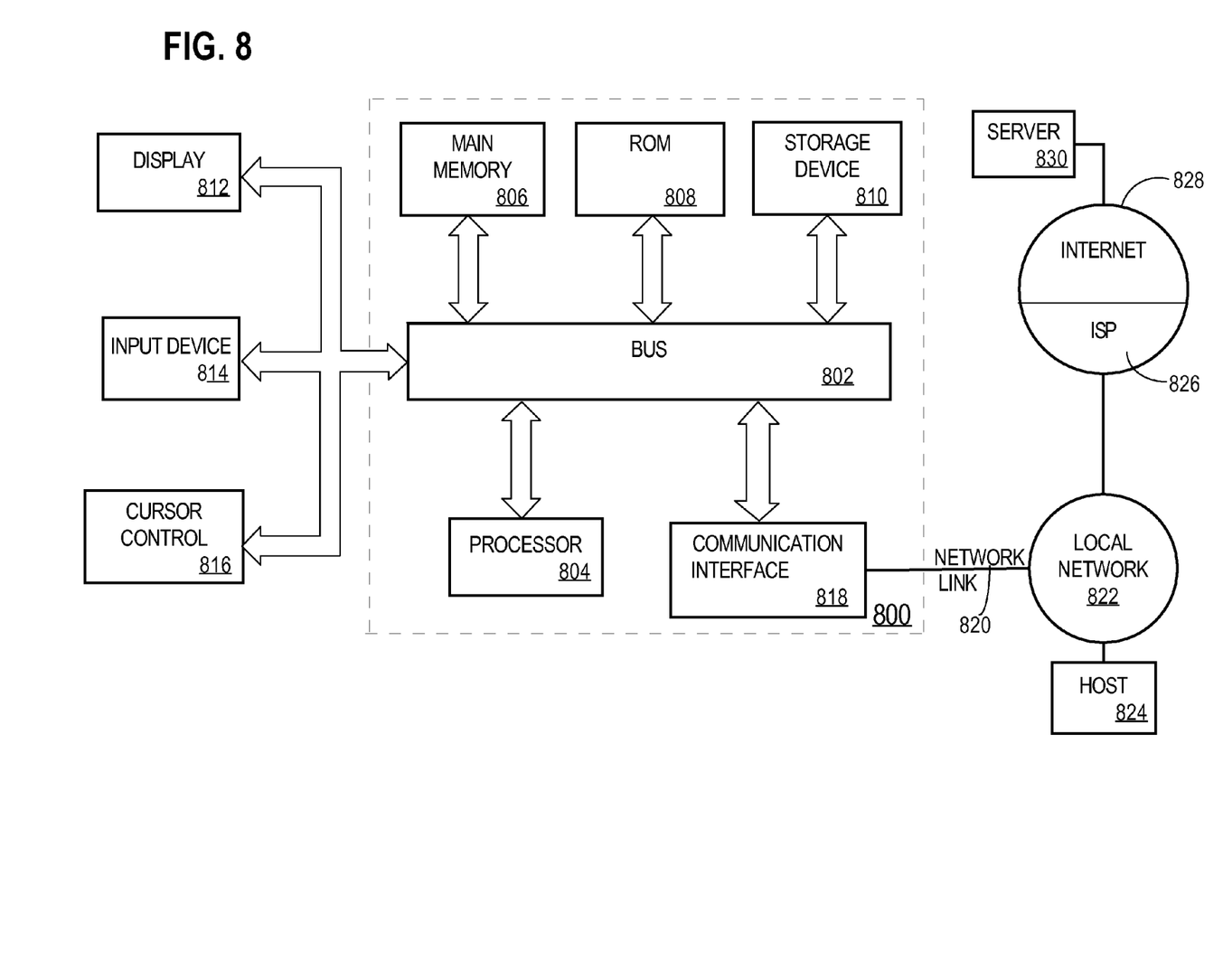
FIG. 8 is a block diagram that depicts a computer system on which embodiments of the invention may be implemented.

For example, FIG. 8 is a block diagram that illustrates a computer system 800 upon which an embodiment of the invention may be implemented. Computer system 800 includes a bus 802 or other communication mechanism for communicating information, and a hardware processor 804 coupled with bus 802 for processing information. Hardware processor 804 may be, for example, a general purpose microprocessor.

Computer system 800 also includes a main memory 806, such as a random access memory (RAM) or other dynamic storage device, coupled to bus 802 for storing information and instructions to be executed by processor 804. Main memory 806 also may be used for storing temporary variables or other intermediate information during execution of instructions to be executed by processor 804. Such instructions, when stored in non-transitory storage media accessible to processor 804, render computer system 800 into a special-purpose machine that is customized to perform the operations specified in the instructions.

Computer system 800 further includes a read only memory (ROM) 808 or other static storage device coupled to bus 802 for storing static information and instructions for processor 804. A storage device 810, such as a magnetic disk, optical disk, or solid-state drive is provided and coupled to bus 802 for storing information and instructions.

Computer system 800 may be coupled via bus 802 to a display 812, such as a cathode ray tube (CRT), for displaying information to a computer user. An input device 814, including alphanumeric and other keys, is coupled to bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane.

Computer system 800 may implement the techniques described herein using customized hard-wired logic, one or more ASICs or FPGAs, firmware and/or program logic which in combination with the computer system causes or programs computer system 800 to be a special-purpose machine. According to one embodiment, the techniques herein are performed by computer system 800 in response to processor 804 executing one or more sequences of one or more instructions contained in main memory 806. Such instructions may be read into main memory 806 from another storage medium, such as storage device 810. Execution of the sequences of instructions contained in main memory 806 causes processor 804 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 810. Volatile media includes dynamic memory, such as main memory 806. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 802. Transmission media can also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid-state drive of a remote computer. The remote computer can load the instructions into its dynamic memory and send the instructions over a telephone line using a modem. A modem local to computer system 800 can receive the data on the telephone line and use an infra-red transmitter to convert the data to an infra-red signal. An infra-red detector can receive the data carried in the infra-red signal and appropriate circuitry can place the data on bus 802. Bus 802 carries the data to main memory 806, from which processor 804 retrieves and executes the instructions. The instructions received by main memory 806 may optionally be stored on storage device 810 either before or after execution by processor 804.

Computer system 800 also includes a communication interface 818 coupled to bus 802. Communication interface 818 provides a two-way data communication coupling to a network link 820 that is connected to a local network 822. For example, communication interface 818 may be an integrated services digital network (ISDN) card, cable modem, satellite modem, or a modem to provide a data communication connection to a corresponding type of telephone line. As another example, communication interface 818 may be a local area network (LAN) card to provide a data communication connection to a compatible LAN. Wireless links may also be implemented. In any such implementation, communication interface 818 sends and receives electrical, electromagnetic or optical signals that carry digital data streams representing various types of information.

Network link 820 typically provides data communication through one or more networks to other data devices. For example, network link 820 may provide a connection through local network 822 to a host computer 824 or to data equipment operated by an Internet Service Provider (ISP) 826. ISP 826 in turn provides data communication services through the world wide packet data communication network now commonly referred to as the "Internet" 828. Local network 822 and Internet 828 both use electrical, electromagnetic or optical signals that carry digital data streams. The signals through the various networks and the signals on network link 820 and through communication interface 818, which carry the digital data to and from computer system 800, are example forms of transmission media.

Computer system 800 can send messages and receive data, including program code, through the network(s), network link 820 and communication interface 818. In the Internet example, a server 830 might transmit a requested code for an application program through Internet 828, ISP 826, local network 822 and communication interface 818.

The received code may be executed by processor 804 as it is received, and/or stored in storage device 810, or other non-volatile storage for later execution.

In the foregoing specification, embodiments of the invention have been described with reference to numerous specific details that may vary from implementation to implementation. The specification and drawings are, accordingly, to be regarded in an illustrative rather than a restrictive sense. The sole and exclusive indicator of the scope of the invention, and what is intended by the applicants to be the scope of the invention, is the literal and equivalent scope of the set of claims that issue from this application, in the specific form in which such claims issue, including any subsequent correction.

What is claimed is:

1. A computing device configured to:
receive authentication information identifying a service provider user;
retrieve, based on the authentication information, a set of one or more documents that are associated with the service provider user;
wherein the set of one or more documents includes a first list of documents and a second list of documents;
wherein the first list is not editable by the service provider user;
wherein the second list is editable by the service provider user;
receive information, from the service provider user, indicating selection of one or more particular documents from the set of one or more documents; and
send, to a repository associated with a client user, document information that at least identifies the one or more particular documents;
wherein the client user is different from the service provider user.

2. The computing device of claim 1 wherein:
a second computing device receives user information identifying the client user;
in response to receiving the user information, the second computing device retrieves, based, at least in part, on the user information, the one or more particular documents from the repository; and
the second computing device causes at least one document of the one or more particular documents to be printed at a printing device communicatively connected to the second computing device.

3. The computing device of claim 2, wherein the second computing device causes the at least one document of the one or more particular documents to be printed in response to the second computing device receiving the user information identifying the client user.

4. The computing device of claim 1, wherein:
the computing device is communicatively connected to a scanner; and
the computing device is further configured to:
cause the scanner to scan a patient identifier code to produce scan data,
wherein the scan data includes a digital representation of the patient identifier code,
identify the client user based on the digital representation of the patient identifier code, and
identify the repository based, at least in part, on the repository being associated with the client user.

5. The computing device of claim 1, wherein the computing device is further configured to:
browse documents, via a network, at a browser;
wherein the browser is configured to receive input from the service provider user that a certain document currently displayed at the browser should be added to the second list of documents; and
in response to receiving the input from the service provider user that the certain document currently displayed at the browser should be added to the second list of documents:
produce print data for the certain document, and
add information for the certain document to the second list of documents,
wherein the information for the certain document includes information for the print data.

6. The computing device of claim 1, wherein:
the one or more particular documents, from the set of one or more documents, are associated with a particular document label; and
the computing device is further configured to receive the information indicating selection of the one or more particular documents by receiving information indicating selection of all documents that are associated with the particular document label.

7. One or more computer-readable media storing instructions which, when processed by one or more processors, cause:
receiving, at a computing device, authentication information identifying a service provider user;
the computing device retrieving, based on the authentication information, a set of one or more documents that are associated with the service provider user;
wherein the set of one or more documents includes a first list of documents and a second list of documents;
wherein the first list is not editable by the service provider user;
wherein the second list is editable by the service provider user;
the computing device receiving information, from the service provider user, indicating selection of one or more particular documents from the set of one or more documents; and
sending, to a repository associated with a client user, document information that at least identifies the one or more particular documents;
wherein the client user is different from the service provider user.

8. The one or more computer-readable media of claim 7 wherein:
a second computing device receives user information identifying the client user;
in response to receiving the user information, the second computing device retrieves, based, at least in part, on the user information, the one or more particular documents from the repository; and
the second computing device causes at least one document of the one or more particular documents to be printed at a printing device communicatively connected to the second computing device.

9. The one or more computer-readable media of claim 8, wherein the second computing device causes the at least one document of the one or more particular documents to be printed in response to the second computing device receiving the user information identifying the client user.

10. The one or more computer-readable media of claim 7, wherein:
the computing device is communicatively connected to a scanner; and
the instructions further comprise instructions for:
the computing device causing the scanner to scan a patient identifier code to produce scan data,
wherein the scan data includes a digital representation of the patient identifier code,
the computing device identifying the client user based on the digital representation of the patient identifier code, and
the computing device identifying the repository based, at least in part, on the repository being associated with the client user.

11. The one or more computer-readable media of claim 7, wherein the instructions further comprise instructions for:
   browsing documents, via a network at the computing device, at a browser;
   wherein the browser is configured to receive input from the service provider user that a certain document currently displayed at the browser should be added to the second list of documents; and
   in response to receiving the input from the service provider user that the certain document currently displayed at the browser should be added to the second list of documents:
      producing print data for the certain document, and
      adding information for the certain document to the second list of documents,
         wherein the information for the certain document includes information for the print data.

12. The one or more computer-readable media of claim 7, wherein:
   the one or more particular documents, from the set of one or more documents, are associated with a particular document label; and
   the instructions further comprise instructions for receiving the information indicating selection of the one or more particular documents by receiving information indicating selection of all documents that are associated with the particular document label.

13. A computer-implemented method comprising:
   receiving, at a computing device, authentication information identifying a service provider user;
   the computing device retrieving, based on the authentication information, a set of one or more documents, that are associated with the service provider user;
   wherein the set of one or more documents includes a first list of documents and a second list of documents;
   wherein the first list is not editable by the service provider user;
   wherein the second list is editable by the service provider user;
   the computing device receiving information, from the service provider user, indicating selection of one or more particular documents from the set of one or more documents; and
   sending, to a repository associated with a client user, document information that at least identifies the one or more particular documents;
   wherein the client user is different from the service provider user.

14. The method of claim 13, wherein:
   a second computing device receives user information identifying the client user;
   in response to receiving the user information, the second computing device retrieves, based, at least in part, on the user information, the one or more particular documents from the repository; and
   the second computing device causes at least one document of the one or more particular documents to be printed at a printing device communicatively connected to the second computing device.

15. The method of claim 13, wherein:
   the one or more particular documents, from the set of one or more documents, are associated with a particular document label; and
   the method further comprises receiving the information indicating selection of the one or more particular documents by receiving information indicating selection of all documents that are associated with the particular document label.

16. The method of claim 15, further comprising:
   browsing documents, via a network at the computing device, at a browser;
   wherein the browser is configured to receive input from the service provider user that a certain document currently displayed at the browser should be added to the second list of documents;
   in response to receiving the input from the service provider user that the certain document currently displayed at the browser should be added to the second list of documents:
      producing print data for the certain document, and
      adding information for the certain document to the second list of documents,
         wherein the information for the certain document includes information for the print data.

* * * * *